United States Patent [19]

Maignan et al.

[11] Patent Number: 5,292,907

[45] Date of Patent: Mar. 8, 1994

[54] PROCESS FOR THE MANUFACTURE OF (6E)-LEUKOTRIENE B4 AND INTERMEDIATES OF THE SAID MANUFACTURING PROCESS

[75] Inventors: Jean Maignan, Tremblay-les-Gonesse; Guy Solladie; Guy Stone, both of Strasbourg, all of France

[73] Assignee: L'Oreal, Paris, France

[21] Appl. No.: 93,752

[22] Filed: Jul. 20, 1993

[30] Foreign Application Priority Data

Jul. 21, 1992 [FR] France .................... 92 08978

[51] Int. Cl.⁵ .................... C07C 51/09; C07C 31/18; C07D 309/00
[52] U.S. Cl. .................... 554/127; 554/126; 554/141; 554/145; 554/146; 554/148; 549/214; 549/273; 556/427; 556/444; 568/23; 568/852; 568/857
[58] Field of Search ............ 554/121, 122, 124, 153, 554/154, 148; 549/214, 415, 416, 420

[56] References Cited

U.S. PATENT DOCUMENTS 4,873,024 10/1989 Abe et al. ..................... 554/153
5,110,949 5/1992 Abe et al. ..................... 549/214

OTHER PUBLICATIONS

Green et al, "Natural acetylenes. Part 59. Synthesis of (−)-(E,S)-dodec-4-ene-6,8,10-triyn-3-ol, the enantiomer of a metabolite of the fungus Peniophora resinosa Jackson and Dearden.", Chem. Abstracts vol. 103, 1985, 141711g.

*Primary Examiner*—Arthur C. Prescott
*Attorney, Agent, or Firm*—Cushman, Darby & Cushman

[57] ABSTRACT

The invention relates to a process for the manufacture of 6-trans-leukotriene B4 (LTB4) of formula

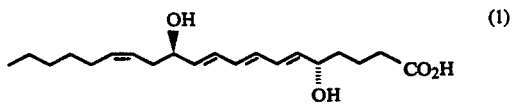

in which a butadienediol is prepared; the hydroxyl groups are esterified to produce a diester and this diester is subjected to a stereospecific reductive elimination using low valency titanium [Ti(0)] to produce a 6-trans triether of formula:

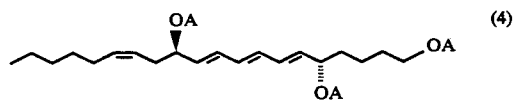

the groups —OA in positions 5 and 12 of which are then converted to —OH groups and the group —CH$_2$OA in position of which is then converted to a —COOH group, to produce 6-trans-LTB$_4$.

The invention also relates to intermediates obtained in the said manufacturing process.

23 Claims, No Drawings

PROCESS FOR THE MANUFACTURE OF (6E)-LEUKOTRIENE B₄ AND INTERMEDIATES OF THE SAID MANUFACTURING PROCESS

The present invention relates to a process for the manufacture of leukotriene B₄, hereinafter denoted by LTB₄, under its 6-trans (also called 6E) configuration and to the intermediates obtained during this manufacture.

It is known that leukotrienes are metabolites of arachidonic acid in leukocytes. Arachidonic acid is converted to an unstable epoxide compound called leukotriene A₄, which is itself converted enzymatically to leukotriene B₄ (LTB₄). LTB₄ causes adhesion and chemotactic movement of leukocytes and stimulates aggregation, release of enzymes and the formation of superoxides in neutrophiles. LTB. is thus implicated in inflammatory processes.

LTB₄ can be prepared with difficulty from natural sources and it is increasingly in demand in pharmacology in the context of biological researches on inflammatory processes.

Attempts have thus been made to prepare LTB. by synthesis but the problem is to obtain a product with a stereochemical structure identical to that of the biological product, that is to say to obtain LTB. in its 6-trans form which has the formula:

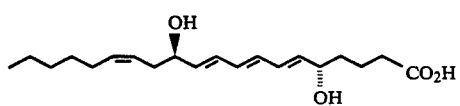
(1)

A large number of processes for the synthesis of leukotrienes have been proposed, for example in J. Amer. Chem. Soc. (1980), 102, 7984; Tetrahedron Letters (1987), 5849; J. Org. Chem. (1990), 55, 5324; Tetrahedron Letters (1983), 24. 409; Tetrahedron Letters (1986), 5857; J. Org. Chem. (1992), 651; Tetrahedron Letters (1981), 1077; J. Amer. Chem. Soc. (1984), 106, 3548; Tetrahedron Letters (1982), 2631; Tetrahedron Letters (1982), 23, 739; Tetrahedron Letters (1986), 27, 4161; J. Org. Chem. (1989), 54, 2409; J. Org. Chem. (1988), 53, 265; J. Org. Chem. (1988), 53, 267 and J. Org. Chem. (1986), 51, 1253.

In all the processes described in the above documents, LTB₄ is obtained in the form of mixtures of isomers, (6E)-LTB. always being present in small proportions.

The report by Corey and coworkers published in Tetrahedron Letters (1981), Vol. 22, No. 17, pages 1587-1590, describes a process for the synthesis of (6E)-LTB₄ by reacting a phosphonium salt of formula:

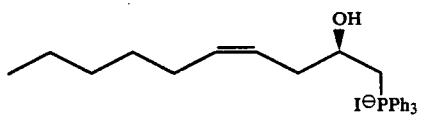

with the diene of formula:

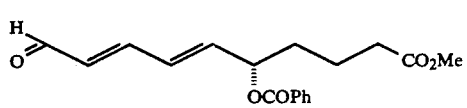

in tetrahydrofuran in the presence of n-butyllithium and hexamethylphosphoric triamide, this reaction being followed by a saponification (in these formulae, Me methyl and Ph=phenyl).

For the implementation of this process, the phosphonium salt is obtained from dimethyl (R,R)-(+)-tartrate by a 9-stage process and the diene is obtained from deoxyribose by an 8-stage process. The synthetic process of Corey is thus a long and expensive process, which does not make it possible to obtain a satisfactory yield. Although the product obtained is stereochemically pure in (6E)-LTB₄, which is better than in the processes mentioned above, it is not yet entirely satisfactory.

The aim of the present invention is to describe a process for the preparation of LTB₄ which is faster, and thus less expensive, and which has a greater 6-trans stereospecificity and a better yield.

The subject of the present invention is thus a process for the preparation of leukotriene B₄ (LTB₄) in the 6-trans (6E) form having the formula:

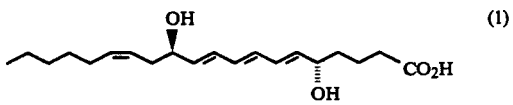
(1)

in which a butadienediol of formula:

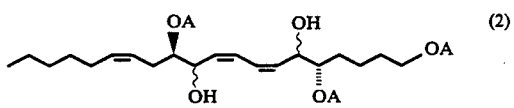
(2)

in which formula A is a silylated protective group, preferably a tert-butyldimethylsilyl group (hereinafter indicated as TBDMS), is prepared; the hydroxyl groups are esterified to produce a group OCOB, B being a phenyl radical or a phenyl radical substituted by a $C_1$–$C_6$ alkyl or alkoxy radical, preferably an unsubstituted phenyl radical, to produce the diester of formula:

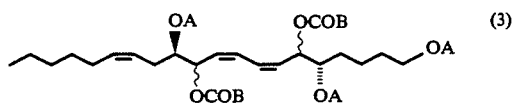
(3)

and the diester of formula (3) is subjected to a reductive elimination using low valency titanium [Ti(0) or an alkali metal amalgam to produce the 6-trans triether of formula:

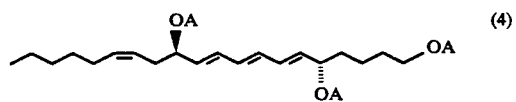
(4)

which is then converted by known processes to 6-trans-LTB₄ by conversion of the groups —OA in positions 5 and 12 to —OH groups and of the group —CH₂OA in position 1 to a —COOH group.

The amalgam of an alkali metal used is preferably a sodium amalgam.

The use of low valency titanium "Ti(0)" obtained by mixing titanium trichloride and lithium aluminium hydride (TiCl₃/LiAlH₄) is known. This low valency titanium is symbolised in the present application by "Ti(0)" although the valency of the titanium is not always exactly 0. It was used for the first time by McMurry [Acc. Chem. Res., Vol. 7, No. 9 (1974)] for the reductive coupling of carbonyl compounds to olefins according to the reaction scheme:

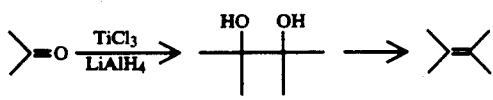

H. M. Walborsky and Wüst H.H. [J. Am. Chem. Soc. (1982), 104, 5807] then used Ti(0) for preparing 1,3-dienes from allylic diols.

The study of the stereochemistry of this reaction and its application to the synthesis of vitamin A and of 13-cis-retinol were described by G. Solladie and others in J. Org. Chem. (1989), 54, 2620. It was observed that, in the synthesis of vitamin A, the reductive elimination process was stereospecific, that is to say that when the starting material is a 13-trans diol, an entirely trans compound is obtained. Likewise, if the starting material is a 13-cis diol, a 13-cis compound is obtained after reduction.

According to the present application, it has now been found that it was possible to stereospecifically reduce a diol derived from a diene, by reduction with Ti(0), to produce a triene provided that the hydroxyl groups of the diol are not free but are blocked in the ester form. In other words, according to the present application, a diene having two conjugated double bonds, of formula:

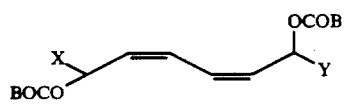

is reacted to produce a triene having three conjugated double bonds:

It was observed that this reduction reaction using low valency titanium [Ti(0)]]was stereospecific, that is to say that, from a 6-trans diene ester of formula (3), the triene triether of formula (4) was obtained in its 6-trans, 8-trans, 10-trans form, with a yield in the region of 99%.

It was also observed that the reduction by an alkali metal amalgam was stereospecific.

According to the invention, the reductive elimination using low valency titanium [Ti(0)] is, preferably, carried out in a solvent, in particular tetrahydrofuran, at a temperature between 50° and 70° C.

According to the invention, the triene triether of formula (4) is preferably converted to 6-trans-LTB4 by the following process:

1) reaction of the triether of formula (4) with a tetra-n-butylammonium fluoride solution in a solvent, in particular tetrahydrofuran, at a temperature between −10° and +20° C. to produce the triol of formula:

2) reaction of the triol of formula (5) with RuCl$_2$(PPh$_3$)$_2$ (where Ph=phenyl), under argon at a temperature of between 10° and 30° C. to produce the lactone of formula:

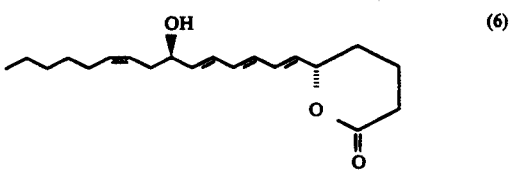

and 3) treatment of the lactone of formula (6) with LiOH in solution in a solvent, in particular tetrahydrofuran, at a temperature below 0° C.

According to the present invention, the butadienediol of formula (2) is preferably prepared by hydrogenation of the diacetylene compound of formula:

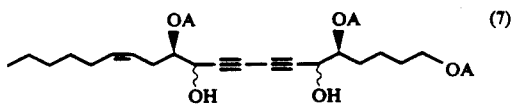

(where A has the same meaning as above) under argon, in the presence of activated Zn in solution in a water/methanol mixture, the diacetylene compound of formula (7) being itself prepared by reaction of the diacetylene compound of formula:

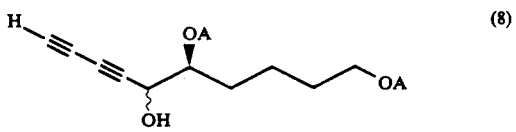

(where A has the same meaning as above), with EtMgBr (where Et=ethyl) in a solvent, in particular tetrahydrofuran, under argon, and then with the aldehyde of formula (9) in solution in a solvent:

The aldehyde of formula (9) is known and its preparation is described in the report by G. Solladié and co-workers, Tetrahedron Asymmetry (1991), Vol. 2, No. 6, pages 457–469, the reaction scheme being given on page 460.

The preparation of the diacetylene compound of formula (8) is advantageously carried out in the following way:

1) reaction of valerolactone with methyl alcohol in the presence of sulphuric acid to produce methyl 5-hydroxypentanoate,
2) etherification of the alcohol functional group to produce the ether of formula:

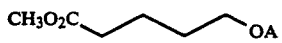 (10)

3) addition of methyl p-tolyl sulphoxide to the ether of formula (10) to produce the sulphoxide of formula (with tol=tolyl):

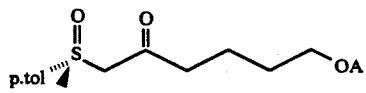 (11)

in the presence of lithium diisopropylamide in solution in a solvent, in particular tetrahydrofuran, at a temperature between −78° C. and 20° C.

4) Reduction of the carbonyl group of the compound of the formula (11) by diisobutylaluminium hydride at a temperature between −70° and −85° C. to produce the sulphoxide of formula:

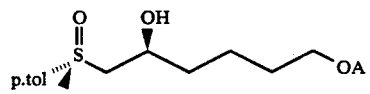 (12)

5) etherification of the alcohol functional group of the sulphoxide of formula (12) by the chlorinated derivative of formula ACl, where A has the same meaning as above, in the presence of imidazole to produce the sulphoxide of formula:

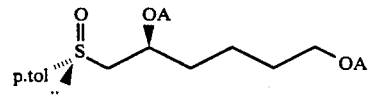 (13)

6) reaction of sodium acetate and acetic anhydride with the compound of formula (13) to produce the acetoxylated derivative of formula (where Ac=acetyl):

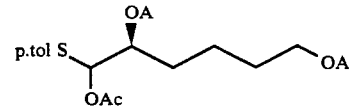 (14)

7) reaction with lithium tri(sec-butyl)borohydride to produce the alcohol of formula:

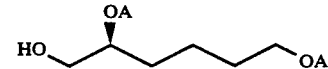 (15)

8) reaction with pyridinium chlorochromate to produce the aldehyde of formula:

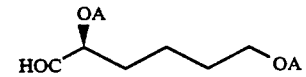 (16)

9) reaction with the compound of formula:

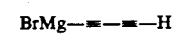

to produce the diacetylene compound of formula (8).

According to the invention, the radical A used is preferably the t-butyldimethylsilyl (TBDMS) radical.

A number of the compounds prepared as intermediates during the preparation procedure are novel. This is the case for the compounds of formula 2 to 4, 7, 8 and to 16 in which A is the t-butylmethylsilyl (TBDMS) radical and B is the phenyl (Ph) radical, for the triol of formula (5) and for the lactone of formula (6).

Consequently, another subject of the present invention is, as novel chemical compounds which are useful as intermediates, the following products (tol=tolyl, Ac=acetyl and TBDMS=t-butyldimethylsilyl, Ph=phenyl):

a) the sulphoxide of formula:

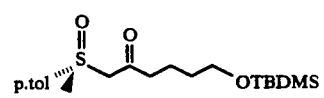 (11)

b) the sulphoxide of formula:

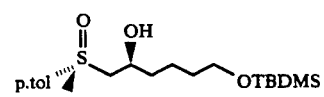 (12)

c) the sulphoxide of formula:

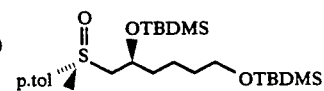 (13)

d) the acetoxylated derivative of formula:

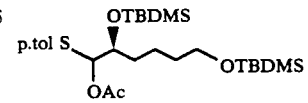 (14)

e) the alcohol of formula:

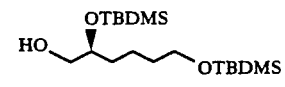 (15)

f) the aldehyde of formula:

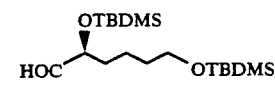 (16)

g) the diacetylene compound of formula:

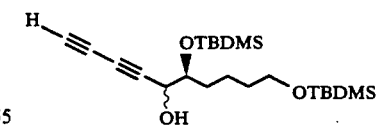 (8)

h) the diacetylene compound of formula:

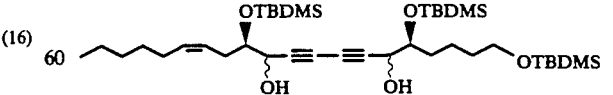 (7)

i) the butadienediol derivative of formula:

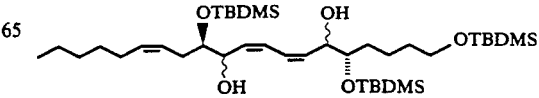 (2)

-continued j) the dibenzoate of formula:

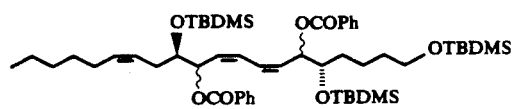

k) the triether of formula:

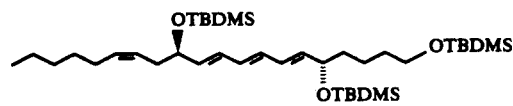

l) the triol of formula:

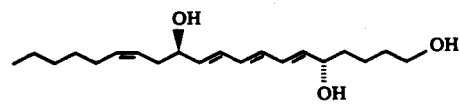

m) the lactone of formula:

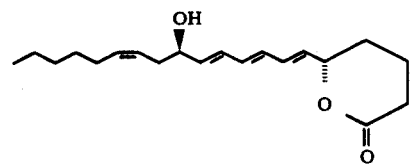

An example of the preparation of (6E)-LTB₄ is given below as purely illustrative and non-limiting.

1st Stage: : Preparation of methyl 5-hydroxypentanoate of formula:

$$H_3CO_2C-(CH_2)_3-CH_2OH \quad (17)$$

10 drops of concentrated H₂SO₄ are added to 10.8 g (0.108 mol) of alpha-valerolactone in 200 ml of dry methanol and the mixture is heated for 6 hours at reflux. 1 g of NaHCO₃ is then added at 0° C. with stirring. After filtration and evaporation of the methanol under vacuum at 25° C., there are obtained 14.2 g (0.108 mol) of the compound of formula (17) in the form of a colourless oil. It was confirmed that the product obtained has the spectral characteristics described in the literature (Huckstep M. and Taylor R. J. K.; Synthesis, 1982, 881).

2nd Stage: Preparation of methyl 5-(t-butyldimethylsilyloxy)pentanoate of formula:

Me = methyl
TBDMS = t-butyldimethylsilyl 17.8 g (0.269 mol, 2.5 equiv) of imidazole and 24.4 g (0.161 mol, 1.5 equiv) of t-butyldimethylsilyl chloride are added to a solution of 14.2 g (0.108 mol) of methyl 5-hydroxypentanoate of formula (17) in 170 ml of dry dimethylformamide under argon and the mixture is stirred for 20 hours under argon. 100 ml of a saturated NH₄Cl solution are then added, with vigorous stirring, and the mixture is extracted twice with an equivalent volume of ether. The organic phases are then washed with saturated NH₄Cl and NaCl solutions, then dried over MgSO₄, filtered on Celite and concentrated under vacuum. The oil obtained is then purified by chromatography (95/5 hexane/ethyl acetate) to give 18.0 g (0.073 mol, yield 68%) of the compound of formula (10) in the form of an oil.

3rd Stage: Preparation of [S-(R)]-6-(t-butyldimethylsilyloxy)-1-p-tolylsulphinyl-2-hexanone of formula:

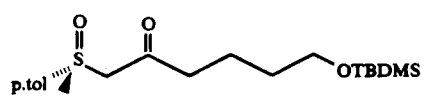

TBDMS = t-butyldimethylsilyl and tol = tolyl p 7.20 g (0.047 mol, 2 equiv) of methyl p-tolyl (+)-(R)-sulphoxide, dissolved in 35 ml of tetrahydrofuran (THF), are added dropwise to a solution of lithium diisopropylamide (0.049 mol, 2.1 equiv) in 100 ml of THF under argon, cooled to −78° C. The resulting yellow solution is stirred for 1 hour at −78° C., then for 30 minutes at 0° C., and cooled again to −78° C. The ester of formula (10) (5.8 g, 0.023 mol, 1 equiv), in solution in 35 ml of THF, is then added over 30 minutes. The resulting solution is slowly reheated and stirred for 2 hours at room temperature. After hydrolysis with 200 ml of a saturated NH₄Cl solution, the mixture is extracted twice with an equal volume of ether and the organic phases washed with saturated NH₄Cl and NaCl solutions, then dried over MgSO₄ and concentrated under vacuum. The crude oil is chromatographed (hexane/ethyl acetate: 50/50) to produce 7.04 g (0.019 mol) of the hexanone of formula (11) in the form of a slightly yellow oil. The yield is 81%.

The characteristics of this product are the following:
a) $R_f = 0.48$ (50% ethyl acetate in hexane);
b) $[\alpha]_D^{24} = +137.7$ (c = 1.6, CHCl₃);
c) IR(CH₂Cl₂) 2850–2920, 1700, 1350, 1090 cn⁻¹;
d) ¹H NMR(CDCl₃) δ: 7.52 (d, J = 8.3 Hz, 2H), 7.31 (d, J = 8.4 Hz, 2H), 3.84 (d, J = 13.5 Hz, 1H), 3.71 (d, J = 13.5 Hz, 1H), 3.56 (t, J = 6.1 Hz, 2H), 2.49 (m, 2H), 2.40 (s, 3H), 1.6–1.4 (m, 4H), 0.86 (s, 9H), 0.02 (s, 6H);
e) ¹³C NMR(CDCl₃) δ: 142.13, 139.72, 130.14, 124.10, 68.12, 62.62, 44.71, 31.83, 25.96, 21.42, 19.62, 18.38, −5.4.

4th Stage: Preparation of [S-(R),(2S)]-6-(t-butyldimethylsilyloxy)-1-p-tolylsulphinyl-2-hexanol of formula:

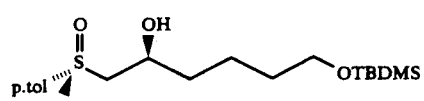

p-tol = p-tolyl
TBDMS = t-butyldimethylsilyl 50 ml of diisobutylaluminium hydride (0.05 mol, 2.7 equiv, 1M solution in toluene) are added dropwise, over 2 hours, to a solution of hexanone of formula (11) (6.85 g, 0.018 mol, 1 equiv) in 170 ml of anhydrous tetrahydrofuran at −78° C. under argon. The mixture is then stirred for 1.5 hours. 10 ml of methanol and 300 ml of ethyl acetate are then added at −78° C. 300 ml of a saturated sodium tartrate solution are then added at room temperature and the mixture is stirred for 30 minutes. The organic phase is separated, washed with saturated NH₄Cl and NaCl solutions, dried over MgSO₄ and concentrated under vacuum. After purification by chromatography (hexane/ethyl acetate: 50/50), the compound of formula (12) is obtained (5.5 g, 0.015 mol, yield 80%) in the form of a yellowish oil. A diastereoisomers ratio equal to 98:2 was determined by H NMR of the crude product. A yield of 87% was calculated taking into account the amount (0.56 g, 1.5 mmol) of unreacted hexanone of formula (11) which can be recycled.

The characteristics of the product obtained are the following:

a) $R_f=0.48$ (60% ethyl acetate in hexane);
b) $[\alpha]_D^{24}= +123.2$ (c=1.9, CHCl$_3$);
c) IR(CH$_2$Cl$_2$) 3650, 3450–3300, 2850–2920, 1100 cm$^{-1}$;
d) $^1$H NMR(CDCl$_3$) δ: main diastereoisomer (98%): 7.50 (d, J=8.2, Hz, 2H), 7.32 (d, J=8.2 Hz, 2H), 4.65 (m, 1H), 3.55 (t, J=6.0 Hz, 2H), 2.98 (dd, J=13.4 and 9.8 Hz, 1H), 2.66 (dd, J=13.3 and 1.6 Hz, 1H), 2.41 (s, 3H), 1.44 (m, 6H), 0.85 (s, 9H), 0.05 (s, 6H); secondary diastereoisomer (2%): 2.85 (dd), 2.71 (dd) and 0.86 (s), 0.018 (s);
e) $^{13}$C NMR(CDCl$_3$) δ: 141.4, 139.6, 130.0, 123.8, 66.4, 62.9, 61.7, 36.7, 32.4, 25.9, 21.4, 21.35, 18.3, 5.35.

5th Stage: Preparation of [S-(R),(2S)]-2,6-bis(t-butyldimethylsilyloxy)-1-(p-tolylsulphinyl)hexane of formula:

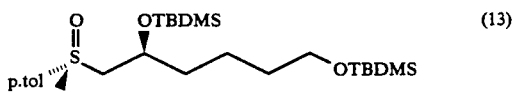

(13)

p-tol=p-tolyl
TBDMS=t-butyldimethylsilyl 5.5 g (14.8 mmol, 1 equiv) of the compound of formula (12) in 60 ml of dry dimethylformamide are added under argon to 2.5 g [37.9 mmol, 2.5 equiv) of imidazole and 3.4 g (22.5 mmol, 1.5 equiv) of t-butyldimethylsilyl chloride and the mixture is stirred for 12 hours. 100 ml of a saturated NH$_4$Cl solution are then added. The aqueous phase is extracted with an equal volume of ether and the organic phases are washed with a saturated NaCl solution, dried over MgSO$_4$ and evaporated. After purification by chromatography (hexane/ethyl acetate: 80/20), the hexane of formula (13) is isolated (7.1 g, 14.6 mmol, yield 98%) in the form of a slightly yellow oil.

The characteristics of this product are the following:
a) R=0.76 (50% ethyl acetate in hexane);
b) $[\alpha]_D^{24}= +125.0$ (c=2.0, CHCl$_3$);
c) IR(CH$_2$Cl$_2$) 2850–2920, 1100 cm$^{-1}$;
d) $^1$H NMR(CDCl$_3$) δ: 7.49 (d, J=8.2 Hz, 2H), 7.29 (d, J=8.2 Hz, 2H), 4.25 (m, 1H), 3.55 (t, J=6.0 Hz, 2H), 2.81 (dd, J=12.9 and 3.1 Hz, 1H), 2.68 (dd, J=12.9 and 9.2 Hz, 1H), 2.39 (s, 3H), 1.6–1.4 (m, 6H), 0.92–0.85 (m, 18H), 0.19–0.05 (m, 2H);
e) $^{13}$C NMR(CDCl$_3$) δ: 141.6, 141.08, 129.9, 123.7, 66.9, 66.5, 62.5, 37.4, 32.8, 25.9, 29.85, 25.65, 20.65, 18.1, −3.59, −4.27, −4.72, −5.35.

6th Stage: Preparation of (2S)-1-acetoxy-2,6-bis(t-butyldimethylsilyloxy)-1-(p-tolylthio)hexane of formula:

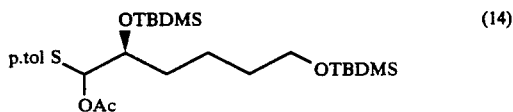

(14)

Ac=acetyl
p-tol=p-tolyl
TBDMS=t-butyldimethylsilyl 4.7 g (57.3 mmol, 4 equiv) of sodium acetate are added to 7.0 g (14.4 mmol, 1 equiv) of the compound of formula (13) in 100 ml of anhydrous acetic acid, under argon, and the mixture is heated at 120° C. for 22 hours. An equivalent volume of toluene is then added and the excess anhydrous acetic acid is removed by azeotropic distillation, the operation being repeated 3 times before adding 200 ml of ether to the residues. The solution is dried over MgSO$_4$, filtered through Celite and the solvent evaporated. After chromatography (hexane/ethyl acetate: 91/9), there are obtained 5.0 g (9.45 mmol, yield 66%) of the compound of formula (14) in the form of a yellow oil. 1.2 g of a byproduct was isolated, which was identified as being the sulphide in which the TBDMS group of the hydroxyl in position 2 had been replaced by an acetate group. By taking into account this byproduct, which can be recycled, the yield of the reaction would be 84%.

The characteristics of the product obtained are the following:

a) $R_f=0.66$ (20% ethyl acetate in hexane);
b) $[\alpha]_D^{24}= +6.0$ (c=1.0, CHCl$_3$);
c) IR(CH$_2$Cl$_2$): 2850–2950, 1730, 1230, 1260, 1110 cm$^{-1}$;
d) $^1$H NMR(CDCl$_3$) δ: 7.35 (dd, J=8.2 and 6.5 Hz, 2H), 7.09 (dd, J=8.2 and 1.8 Hz, 2H), 6.09 (d, J=2.3 Hz, 0.5H), 6.01 (d, J=6.4 Hz, 0.5H), 3.91 (ddd, J=7.2, 7.1 and 2.3 Hz, 0.5H), 3.81 (dd, J=11.5 and 6.2 Hz, 0.5H), 3.60 (m, 2H), 2.18 (d, J=3.6 Hz, 3H), 2.1 (s, 3H), 1.38 (m, 2H), 1.25 (m, 4H), 0.89 (m, 18H), 0.06 (m, 12H);
e) $^{13}$C NMR(CDCl$_3$) δ: mixture of diastereoisomers 169.6, 169.2, 137.8, 137.95, 133.72, 132.89, 129.74, 129.72, 128.52, 129.3, 86.72, 84.05, 74.5, 72.76, 63.04, 62.99, 33.64, 33.11, 33.03, 32.84, 25.81, 25.97, 25.75, 22.06, 21.21, 21.15, 21.1, 20.99, 18.0, −4.5, −4.6, −5.3.

7th Stage: Preparation of (2S)-2,6-bis(t-butyldimethylsilyloxy) hexan-1-ol of formula:

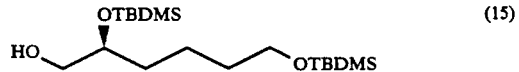

(15)

TBDMS=t-butyldimethylsilyl 36 ml (1M solution/THF, 36.0 mmol, 4 equiv) of lithium tri(sec-butyl)borohydride, sold under the commercial name "L-Selectride" by the company "Aldrich", are added dropwise to a solution of 4.8 g (9.07 mmol, 1 equiv) of the compound of formula (14) in 180 ml of tetrahydrofuran (THF), cooled to −78° C. At the end of the addition, the mixture is slowly reheated to room temperature and stirred for 1.5 hour. The mixture is cooled again to −78° C. and 20 ml of methanol are gently added. The mixture is left to return to room temperature, several spatulas of SiO$_2$ are added and the mixture is stirred for a further 1 hour before filtering on Celite. The solvent is evaporated and purification is carried out by chromatography (hexane/ethyl acetate: 89/11). 2.44 g (6.70 mmol) of the alcohol of formula (15) are collected in the form of an oil. The yield is 74%.

The product obtained has the following characteristics:

a) $R_f=0.35$ (11% ethyl acetate in hexane);
b) IR(CHCl$_3$): 3400, 2840–2905, 1450 cm$^{-1}$;
c) $^1$H NMR(CDCl$_3$) δ: 3.73 (m, 1H), 3.60 (t, J=6.1 Hz, 2H), 3.56 (dd, J=7.9 and 3.9 Hz, 1H), 3.43 (dd, J=11.5 and 5.7 Hz, 1H), 1.72 (broad m, 1H), 1.55-1.4 (m, 6H), 0.89 (m, 18H), 0.01 (m, 12H);

d) $^{13}$C NMR(CDCl$_3$) δ: 72.89, 66.25, 62.98, 33.78, 32.97, 25.96, 25.85, 21.69, 18.34, 17.60, −4.40, −4.56, −5.32.

8th Stage: Preparation of (2S)-2,6-bis(t-butyldimethylsilyloxy) hexan-1-al of formula:

(16)

TBDMS = t-butyldimethylsilyl 3.4 g (15.8 mmol, 2.6 equiv) of pyridinium chloroformate (PCC) are added to a solution of 2.2 g (6.04 mmol, 1 equiv) of the compound of formula (15) in 120 ml of dry CH$_2$Cl$_2$, under argon, in the presence of 4Å molecular sieves. After 4 hours, 200 ml of ether are added and filtration is carried out through Celite. After evaporating the solvent and chromatography (hexane/ethyl acetate: 89/11), 1.88 g (5.19 mmol) of the aldehyde of formula (16) are isolated in the form of a slightly yellow oil; the yield is 86%.

The product obtained has the following characteristics:

a) R$_f$=0.68 (11% ethyl acetate in hexane);
b) [α]$_D^{24}$= −21.6 (c=0.85, CHCl$_3$);
c) IR(CHCl3): 2840–2905, 1720, 1450, 1380, 1090 cm$^{-1}$;
d) $^1$H NMR(CDCl$_3$) δ: 9.52 (d, J=1.7 Hz, 1H), 3.96 (dt, J=5.7 and 1.6 Hz, 1H), 3.60 (t, J=5.9 Hz, 2H), 1.6-1.4 (m, 6H), 0.89 (m, 18H), 0.02 (m, 12H);
e) $^{13}$C NMR(CDCl$_3$) δ: 198.5, 77.7, 62.81, 32.64, 32.46, 5.92, 25.73, 21.19, 18.17, −4.6, −4.9, −5.3.

9th Stage: Preparation of (6S)-6,10-bis(t-butyldimethylsilyloxy)-5-hydroxy-1,3-decadiyne of formula:

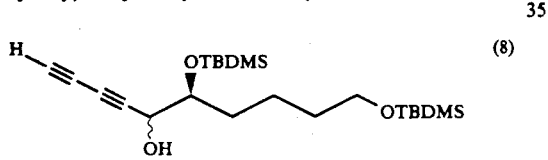
(8)

TBDMS = t-butyldimethylsilyl 10 ml of a 1M solution of ethylmagnesium bromide in ether (10.0 mmol, 2 equiv) are added to 1.0 g (20.0 mmol, 4 equiv) of diacetylene in 20 ml of dry tetrahydrofuran, cooled to −78° C., so as to obtain the compound of formula:

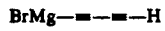
BrMg—≡—≡—H

The solution is then stirred for 1.5 hours at room temperature. It is again cooled to −78° C. and the aldehyde of formula (16) (1.8 g, 4.97 mmol, 1 equiv), in solution in 15 ml of ether, is added over a period of 20 minutes. Stirring is then carried out for 1 hour at 0° C., hydrolysis is carried out with 100 ml of a saturated NH$_4$Cl solution and extraction is carried out three times with ether. The organic phases are washed with saturated NH$_4$Cl and NaCl solutions, dried over MgSO$_4$, concentrated under vacuum and chromatographed (hexane/ethyl acetate: 89/11). 1.69 g (4.10 mmol) of the diacetylene derivative of formula (8) are obtained in the form of an oil, which rapidly darkens. The yield is 82%.

The product obtained has the following characteristics:

a) R$_f$=0.41 (11% ethyl acetate in hexane);
b) [α]$_D^{24}$= +3.4 (c=0.88, CHCl$_3$);
c) IR(CHCl$_3$): 3500 (broad), 3290 (narrow), 2840–2905, 1450, 1350, 1100 cm$^{-1}$;
d) $^1$H NMR(CDCl$_3$) δ: 4.35 (d, J=3.5 Hz, 0.6 H), 4.25 (d, J=3.3. Hz, 0.4H), 3.75 (m, 1H), 3.60 (dt, J=6.2 and 2.1 Hz, 2H), 2.15 (m, 1H), 1.6-1.3 (m, 6H), 0.85 (m, 18H), 0.2–0.0 (m, 12H);
e) $^{13}$C NMR(CDCl$_3$) δ: 75.1, 74.8, 67.95, 67.9, 66.3, 64.9, 62.85, 33.48, 32.8, 32.4, 25.96, 25.82, 25.8, 21.64, 21.48, 18.06.

10th Stage : Preparation of [4Z, 2(R)]-2-(t-butyldimethylsilyloxy)-4-decen-1-al of formula:

(9)

TBDMS = t-butyldimethylsilyl

The aldehyde of formula (9) is prepared by the process described in pages 461 to 465 of the publication "Tetrahedron Asymmetry, Vo. 2, No. 6, pages 457–468", according to the scheme:

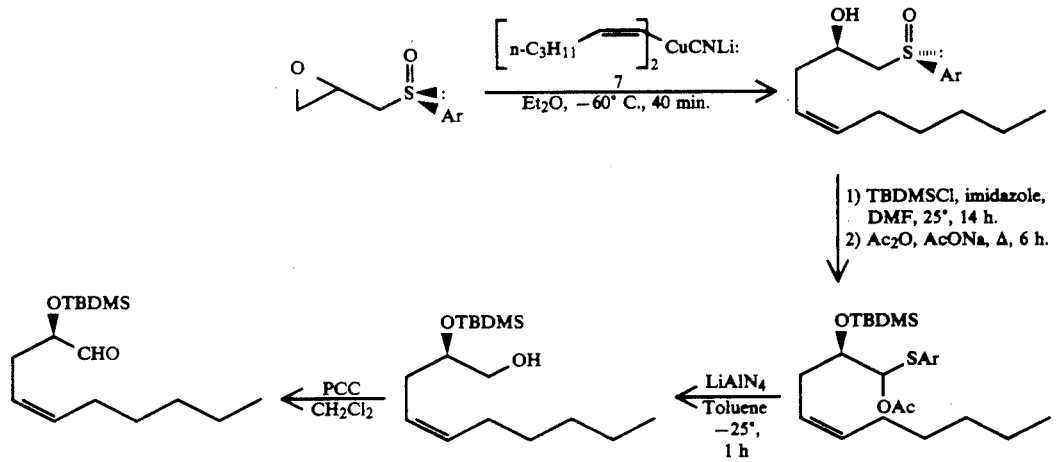

in which formulae:
Ar=p-tolyl
Et=ethyl
TBDMS=t-butyldimethylsilyl
DMF=dimethylformamide
Ac=acetyl
PCC=pyridinium chlorochromate 11th Stage: Preparation of (14Z,5S,12R)-1,5,12-tris(t-butyldimethylsilyloxy)-6,11-bishydroxy-14-eicosene-7,9-diyne of formula:

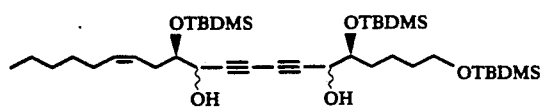

TBDMS = t-butyldimethylsilyl

The diacetylene compound of formula (8) (0.58 g, 1.41 mmol, 1 equiv), in solution in 5 ml of tetrahydrofuran (THF), is treated at 0° C. with $C_2H_5MgBr$ (1M in ether, 3.0 ml, 2.1 equiv) and is then stirred at room temperature for 1.5 hour. The mixture is again cooled to 0° C. and the aldehyde of formula (9) (0.4 g, 1.41 mmol, 1 equiv), dissolved in 2 ml of THF, is added dropwise over a period of 10 minutes. The mixture is then stirred at room temperature for 3 hours, hydrolysed with 10 ml of a saturated $NH_4Cl$ solution and extracted three times with ether. The organic phases are finally washed with saturated $NH_4Cl$ and NaCl solutions, dried over $MgSO_4$, concentrated and the residue is purified by chromatography (hexane/ethyl acetate: 94/6). 0.63 g (0.90 mmol) of the diacetylene compound of formula (7) are collected in the form of a yellow oil with a yield of 63%. A yield of 89% can be calculated, if the unreacted diacetylene compound of formula (8) (0.16 g, 0.39 mmol) is recycled.

The characteristics of the product obtained are the following:

a) $R_f=0.34$ (11% ethyl acetate in hexane);

b) $^1H$ NMR($CDCl_3$) δ: 5.50 (m, 1H, H15), 5.45 (m, 1H, H14), 4.37 (t, J=3.6 Hz, 1H, H12), 4.27 (t, J=3.2 Hz, 1H, H5), 3.77 (m, 2H, H6,11), 3.60 (dt, J=6.1 and 1.3 Hz, 2H, H1), 2.38 (m, 2H, H13), 2.03 (m, 2H, H16), 1.60–1.45 (m, 6H), 1.30 (m, 6H), 0.90 (m, 30H), 0.10 (m, 18H).

12th Stage: Preparation of (7Z,9Z,14Z,5S,12R)-1,5,12-tris (t-butyldimethylsilyloxy)-6, 11 -bishydroxy-7,9,14-eicosatriene of formula:

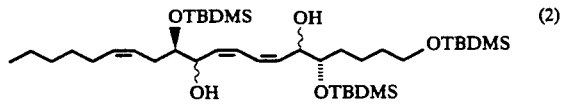

TBDMS = t-butyldimethylsilyl

First of all, activated zinc is prepared according to the method described by W. Bolland and coworkers; Helv. Chim. Acta, 1987, 70, 1025. Zinc powder (6.3 g, 96.9 mmol) in 40 ml of distilled water is stirred for 15 minutes under argon. Copper acetate $Cu(OAc)_2$ (0.57 g, 3.13 mmol) is then added and the mixture is again stirred for 15 minutes under argon. $AgNO_3$ (0.63 g, 3.70 mmol) is then added and the mixture is stirred for 30 minutes. Filtration is carried out and the activated zinc is washed successively with distilled water, methanol, acetone and ether. The activated zinc is then transferred to a round-bottomed flask containing 25 ml of a mixture (methanol/$H_2O$: 1/1) under argon. The diacetylene compound of formula (7), dissolved in 4 ml of methanol, is added. The reaction is monitored by thin layer chromatography. After stirring for 32 hours, 50 ml of methanol are added, and the zinc is filtered and washed carefully with methanol. After evaporation of the methanol, the residue is taken up in ether and dried over $MgSO_4$. After evaporation of the solvent, the product is purified by chromatography (hexane/ethyl acetate: 91/9). The triene of formula (2) obtained (0.50 g, 0.72 mmol) exists in the form of an oil and is a mixture of two diastereoisomers, corresponding to the two OH groups in positions 6 and 11, in the ratio 1/1.3. The yield is 79%.

The diastereoisomers obtained have the following characteristics:

a) $R_f=0.50$ (secondary) and 0.26 (main) (14% ethyl acetate in hexane);

b) $[\alpha]_D^{24} = +6.4$ (c=1.7, $CHCl_3$);

c) IR($CHCl_3$) 3550, 2860–2905, 1450, 1190 cm$^{-1}$;

d) $^1H$ NMR($CDCl_3$) δ: secondary diastereoisomer: 6.35 (m, 2H, H8,9, d with J=11.2 after irradiation of m at 5.45 ppm), 5.60-5.30 (m, 4H, H7,10,14,15), 4.56 (m, 1H, H11), 4.41 (dd, J=3.7 and 8.6 Hz, 1H, H6), 3.74 (m, 2H, H5,12), 3.58 (m, 2H, H1), 2.20 (m, 2H, H13), 2.00 (m, 2H, H16), 1.48 (m, 6H), 1.26 (m, 6H), 0.89 (m, 30H), 0.05 (m, 18H); main diastereoisomer: 6.35 (m, 2H, H8,9), 5.60-5.30 (m, 4H, H7,10,14,15), 4.53 (dd, J=8.9 and 3.2 Hz, 1H, H11), 4.42 (m, 1H, H6), 3.74 (m, 1H, H12), 3.59 (m, 3H, H1,5), 2.50-2.20 (m, 2H, H13), 2.00 (q, J=7.2 Hz, 2H, H16), 1.50-1.25 (m, 12H), 0.89 (m, 30H), 0.05 (m, 18H).

13th Stage: Preparation of (7Z,9Z,14Z,5S,12R)-1,5,12-tris (t-butyldimethylsilyloxy)-6,11-bisbenzoxy-7,9,14-eicosatriene of formula:

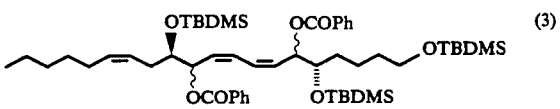

TBDMS = t-butyldimethylsilyl
Ph = phenyl 0.21 ml of benzoyl chloride (1.8 mmol, 2.25 equiv) are added to the mixture of the two diastereoisomers of formula (2) (0.502 g, 0.72 mmol, 1 equiv) in solution in 12 ml of anhydrous pyridine and under argon. After reacting for 12 hours, 100 ml of ether are added, and washing is carried out twice with an equal volume of 5% $H_2SO_4$, saturated $NaHCO_3$ and saturated NaCl respectively. The organic phase is dried over $MgSO_4$ and the solvent evaporated. After chromatography (hexane/ethyl acetate: 94/6), 0.56 g (0.62 mmol) of the dibenzoate of formula (3) is isolated in the form of two diastereoisomers in the ratio 1/1.04. The product exists in the form of an oil. The yield is 86%. The two diastereoisomers can be separated by chromatography.

The diastereomers obtained have the following characteristics:

a) $R_f = =0.34$ (secondary) and 0.30 (main) (6% ethyl acetate in hexane);

b) $[E]_D^{24} = 22.2$ (c=1.2 $CHCl_3$);

c) IR($CHCl_3$) 2840–2900, 1700, 1450, 1250, 1100 cm$^{-1}$;

d) $^1H$ NMR($CDCl_3$) δ: secondary diastereoisomer: 8.1 (m, 4H), 7.5 (m, 6H), 6.68 (m, 2H), 6.0–5.60 (m, 4H), 5.45 (m, 2H), 4.00 (m, 2H), 3.55 (t, J=6.0 Hz, 2H), 2.24 (m, 2H), 1.90 (t, J=6.5 Hz, 2H), 1.50 (m, 6H), 1.20 (m, 6H), 0.89 (m, 30H), 0.05 (m, 18H); main diastereoisomer 8.1 (m, 4H), 7.49 (m, 6H), 6.86 (dd, J=11.6 and 9.6 Hz, 1H), 6.71 (m, 1H), 5.95 (dd, J=11.2 and 3.5 Hz, 2H), 5.75 (m, 2H), 5.45 (m, 2H), 4.00 (m, 2H), 3.58 (m, 2H), 2.25 (m, 2H), 2.00 (m, 2H), 1.50 (m, 6H), 1.28 (m, 6H), 0.92 (m, 30H), 0.05 (m, 18H).

14th Stage: Preparation of (6E,8E,10E,1Z,5S,12R)-1,5,12-tris (t-butyldimethylsilyloxy)-6,8,10,14-eicosatetraene of formula:

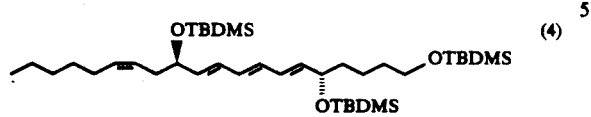

TBDMS = t-butyldimethylsilyl

A suspension of "Ti(0)" was prepared according to the process described in Walborsky et al., J. Amer. Chem. Soc., 1982, 104, 5807. 15 ml of anhydrous tetrahydrofuran (THF) are added slowly to TiCl3 (0.50 g, 3.2 mmol, 2 equiv) in a very dry, round-bottomed flask, under argon. LiAlH4 (1.6 ml of a 1M solution in ether, 1.6 mmol, 1 equiv) is then gently added. The mixture rapidly becomes black. The remainder of the reaction, including chromatography of the product, is carried out in the absence of UV light in a laboratory lit by yellow light. After 30 minutes, 2.6 ml of this suspension of "Ti(0)" (approximately 0.57 mmol, 6 equiv) are transferred to a round-bottomed flask equipped with a cooling medium and under argon. The dibenzoate of formula (3), in the form of a mixture of diastereoisomers (0.087 g, 0.096 mmol, 1 equiv) in 1 ml of THF, is then added with a syringe to the suspension of "Ti(0)". The reaction mixture is then immersed in a bath heated at 65° C. After 20 minutes, thin layer chromatography shows the reaction is complete. The mixture is then cooled to 0° C., H2O (1 ml) and 0.75% HCl (10 ml) are successively added and extraction is carried out three times with 100 ml of ether. The organic phases are successively washed with 0.75% HCl, saturated NaHCO3 and saturated NaCl, then dried over MgSO4 and evaporated. The NMR of the crude product shows that it is virtually pure. After chromatography (hexane/ethyl acetate: 96/4), 0.063 g (0.094 mmol) of the triene of formula (4) is isolated in the form of an oil. The yield is 99%.

The product obtained has the following characteristics:

a) $R_f$=0.71 (6% ethyl acetate in hexane);
b) $[\alpha]_D^{24}$= +13.1 (c=0.87, CHCl3);
c) IR(CHCl3): 2840-2905, 1625 , 1430, 1380, 1275 cm$^{-1}$;
d) $^1$H NMR(CDCl3) δ: 6.15 (m, 4H, H7,8,9,10 after decoupling of m at 5.69 ppm), 5.69 (m, 2H, H6,11, d with J=15.5 Hz after decoupling of m at 4.15 ppm), 5.47 (m, 1H, H15, d with J=11 Hz after decoupling of m at 2.0 ppm), 5.34 (m, 1H, H14, d with J=11 Hz after decoupling of m at 2.3 ppm), 4.15 (q, J=7.0 Hz, 2H, H5,12), 3.59 (t, J=3.2 Hz, 2H, H1), 2.28 (m, 2H, H13), 2.00 (m, 2H, H16), 1.50 (m, 6H), 1.30 (m, 6H), 0.90 (m, 30H), 0.06 (m, 18H);
e) $^{13}$C NMR(CDCl3) δ: 137.26, 136.71, 131.91, 131.73, 129.35, 129.26, 125.51, 125.12, 73.2, 63.14, 38.2, 36.4, 32.8, 31.55, 30.32, 29.31, 27.44, 25.97, 25.90, 22.59, 21.58, 18.36, 18.27, 18.24, 14.09, −4.28, 4.40, −4.75, −4.79, −5.28.

15th Stage: Preparation of (6E,8E,10E,14Z,5S,12R)-1,5,12-trishydroxy-6,8,10,14-eicosatetraene of formula:

A 1M solution of tetra-n-butylammonium fluoride in tetrahydrofuran (THF) (0.56 ml, 6 equiv) is added at 0° C. to the triene of formula (4) (0.063 g, 0.094 mmol, 1 equiiv) in 5 ml of THF. The solution is then stirred for 3 hours at room temperature and then diluted with 50 ml of ether. The organic phase is then washed with a saturated NaCl solution and the aqueous phase is extracted twice with ether. After drying over MgSO4 and evaporation of the solvents, the product is chromatographed (hexane/ethyl acetate: 25/75). There is obtained 0.030 g (0.094 mmol) of the triol of formula (5), i.e. a yield of 99%. The product is in the form of an oil.

The characteristics of the product obtained are the following:

a) $R_f$=0.25 (75% ethyl acetate in hexane);
b) $[\alpha]_D^{24}$= +12.4 (c=0.95, CHCl3);
c) $^1$H NMR(CDCl3) δ: 6.19 (m, 4H, H7,8,9,10, s after decoupling of m at 5.71 ppm), 5.71 (dd, J=14.6 and 5.9 Hz, 2H, H6,11) 5.54 (m, 1H, H15, d with J=10.6 Hz after decoupling of m at 2.1 ppm), 5.37 (m, 1H, H14, d with J=10.6 Hz after decoupling of m at 2.3 ppm), 4.17 (m, 2H, H5, 12), 3.62 (t, J'6.2 Hz, 2H, H1), 2.30 (m, 2H, H13), 2.15 (m, 2H, H(OH)), 2.10 (m, 2H, H16), 1.55 (m, 4H), 1.28 (m, 8H), 0.90 (t, J=6.8 Hz, 3H);
d) $^{13}$C NMR(CDCl3) δ: 137.64, 136.64, 134.48, 132.97, 132.84, 131.05, 130.9, 124.8, 73.17, 72.6, 63.33, 37.5, 36.01, 32.12, 32.17, 29.95, 28.09, 23.23, 22.26, 14.74.

16th Stage: Preparation of the (6E, 8E, 10E, 14Z, 5S, 12R)-12-hydroxy-6, 8,10,14-eicosatetraene-(1,5)-lactone of formula:

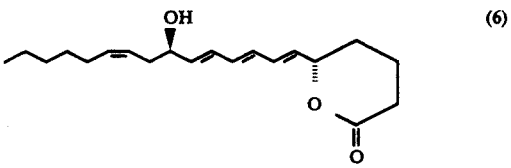

The triol of formula (5) (0.01 g, 0.03 mmol, 1.25 equiv) in 1 ml of benzene is added to RuCl2(PPh3)2. prepared according to Tomioka et al., Tetrahedron Letters, 1981, 22, 1605 (0.024 g, 0.025 mmol, 1 equiv) (with Ph=phenyl) under argon. After reacting for 2 hours, 25 ml of ether are added and the mixture is filtered on silica. Purification by preparative thin layer chromatography (hexane/ethyl acetate: 50/50) leads to 7.1 mg (0.020 mmol) of the lactone of formula (6). The product is in the form of an oil. The yield is 70%.

The characteristics of the product obtained are the following:

a) $R_f$=0.34 (50% ethyl acetate in hexane);
b) $[\alpha]_D^{24}$= +8.03 (c=0.85 CHCl3);
c) IR(CHCl3): 3550, 2860-2910, 1715, 1450, 1100 cm$^{-1}$;
d) $^1$H NMR(CDCl3) δ: 6.39 (m, 1H, H7), 6.25 (m, 3H, H8,9,10, s after decoupling of m at 5.75 ppm), 5.80 (m, 1H, H11), 5.69 (dd, J=15.0 and 6.2 Hz, 1H, H6), 5.55 (m, 1H. H15, d with J=11.0 Hz after decoupling of m at 2.0 ppm), 5.40 (m, 1H, H14, d with J=11.0 Hz after decoupling of m at 2.45 ppm), 4.88 (m, 1H, H5), 4.24 (q, J=5.7 Hz, 1H, H12), 2.55 (m, 2H, H2), 2.32 (t, J=6.8

Hz, 2H, H13), 2.05 (m, 2H, H16), 1.95 (m, 2H, H4), 1.55 (m, 2H), 1.25 (m, 6H), 0.90 (t, J=7.0 Hz, 3H).

17th Stage: Preparation of 6-trans-leukotriene B4 of formula:

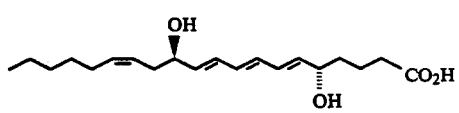

A 0.35 M solution in water of LiOH (0.15 ml, 0.05 mmol, 1.1 equiv) is added, under argon and at $-10°$ C., to a solution of the lactone of formula (6) (14.8 mg, 0.046 mmol, 1 equiv) in 1 ml of tetrahydrofuran. The reaction is complete in 20 minutes. After two extractions with $CH_2Cl_2$, washing with a saturated NaCl solution, drying over $MgSO_4$ and evaporation of the solvents, the product is purified by preparative thin layer chromatography (ethanol/ethyl acetate: 11/89). There are obtained 7.0 mg (0.021 mmol) of 6-trans-LTB4, which exists in the form of a white solid. The yield is 45%.

The product obtained has the following characteristics:

a) $R_f$=0.40 (11% of ethanol in ethyl acetate);
b) $[\alpha]_D^{24}$= +11.2 (c=2.0, $CHCl_3$);
c) IR($CH_2Cl_2$: 3600-3200 (broad), 3024, 3014, 2860, 1710 (narrow), 1456, 1378, 1242, 1232, 1092 $cm^{-1}$;
d) UV $I_{max}$ (methanol): 256.5, 266.0, 277.0 (abs 0.675, 0.896 and 0.712 respectively) (values given in E. J. Corey et al. in Tetrahedron Letters [1981], 22, 1587 :(methanol) 258, 268, 280);
e) $^1$H NMR($CDCl_3$) δ: 6.27 (m, 1H, H7), 6.21 (m, 3H, H8,9,10), 5.74 (m, 2H, H6,11, dd with J=14.6 and 7.7 Hz after decoupling at 4.19 ppm), 5.58 (m, 1H, H15, d with J=11.0 Hz after decoupling of m at 2.1 ppm), 5.34 (m, 1H, H14, dd with J=10.6 Hz after decoupling of m at 2.35 ppm), 4.19 (m, 1H, H5,12), 2.35 (m, 4H, H2,13), 2.10 (m, 2H, H16), 1.65 (m, 4H), 1.36 (m, 6H), 0.90 (t, J=7 Hz, 3H).

We claim:

1. Process for the preparation of leukotriene B4 (LTB4) in the 6-trans (6E) form, having the formula:

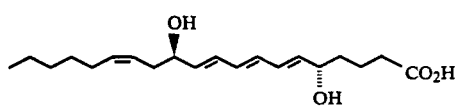

characterized in that a butadienediol of formula:

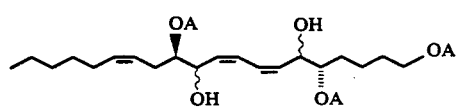

in which A is a silylated protective group, is prepared; the hydroxyl groups are esterified to produce a group OCOB, B being a phenyl radical or a phenyl radical substituted by a $C_1$-$C_6$ alkyl or alkoxy radical, to produce the diester of formula:

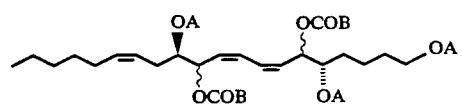

and this diester is subjected to a reductive elimination using low valency titanium [Ti(0)] or an alkali metal amalgam to produce the 6-trans triether of formula:

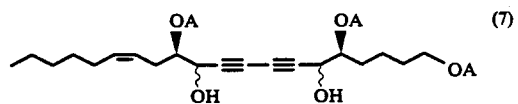

the groups —OA in positions 5 and 12 of which are then converted to 13 OH groups, and the group —$CH_2OA$ in position 1 of which is then converted to a —COOH group, to produce 6-trans-LTB4.

2. Process according to claim 1, characterized in that A is a t-butyldimethylsilyl group.

3. Process according to claim 1 characterised in that B is a phenyl radical.

4. Process according to claim 1 characterised in that the reductive elimination with low valency titanium is carried out in a solvent, at a temperature of between 50° and 70° C.

5. Process according to claim 4, characterised in that the solvent is tetrahydrofuran.

6. Process according to claim 1 characterised in that the triether of formula (4) is converted to (6E)-LTB4 by the following stages:

a) reaction of the 6-trans triether of formula (4) with a tetra-n-butylammonium fluoride solution in a solvent, at a temperature between $-10°$ and $+20°$ C., to produce the triol of formula:

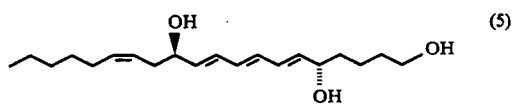

b) reaction of the triol of formula (5) with $RuCl_2(PPh_3)_2$ (with Ph=phenyl), under argon, at a temperature between 10° and 30° C. to produce the lactone of formula:

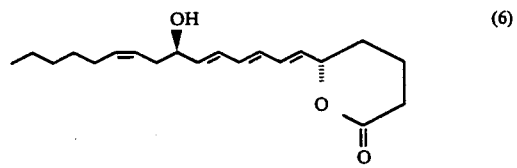

and c) treatment of the lactone of formula (6) with LiOH in solution in a solvent at a temperature of less than 0° C.

7. Process according to claim 6, characterised in that the solvent used in Stages a and/or c of claim 6 is tetrahydrofuran.

8. Process according to claim 1 characterised in that the butadienediol of formula (2 ) is prepared by hydrogenation of the diacetylene compound of formula:

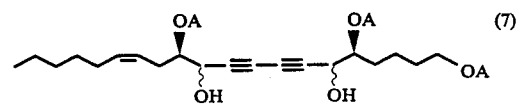

where A has the same meaning as in claim 1, under argon, in the presence of activated Zn in solution in a water/methanol mixture, the diacetylene compound of formula (7) being itself prepared by reaction of the diacetylene compound of formula:

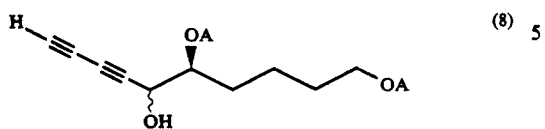

where A has the same means as in claim 1, with C$_2$H$_5$MgBr in a solvent, under argon, and then with the aldehyde of formula (9) in solution in a solvent:

9. Process according to claim 8, characterised in that the solvent is tetrahydrofuran.

10. Process according to claim 1 characterised in that the diacetylene compound of formula (8) is prepared by the following stages:
   a) reaction of valerolactone with methyl alcohol in the presence of sulphuric acid to produce methyl 5-hydroxypentanoate;
   b) etherification of the alcohol functional group to produce the ether of formula:

where A has the same meaning as in claim 1;
   addition of methyl p-tolyl sulphoxide to the ether of formula (10) to produce the sulphoxide of formula (11) (with tol=tolyl):

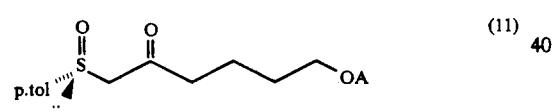

in the presence of lithium diisopropylamide in solution in a solvent at a temperature between −78° C. and 20° C.;
   d) reduction of the carbonyl group of the compound of the formula (11) by diisobutylaluminium hydride at a temperature between −70° and −85° C. to produce the sulphoxide of formula:

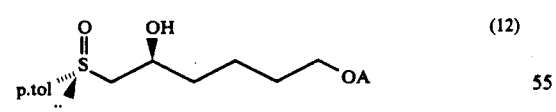

e) etherification of the alcohol functional group of the sulphoxide of formula (12) by the chlorinated derivative of formula ACl where A has the same meaning as in claim 1, in the presence of imidazole to produce the sulphoxide of formula:

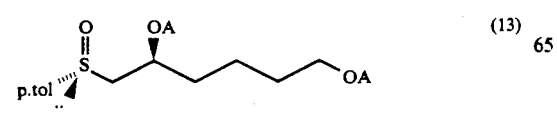

f) reaction of sodium acetate and acetic anhydride with the sulphoxide (13) to produce the acetoxylated derivative of formula (where Ac=acetyl):

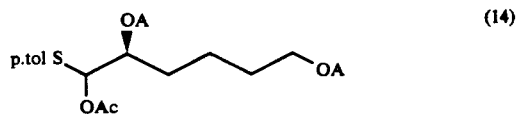

g) reaction with lithium tri(sec-butyl)borohydride to produce the alcohol of formula:

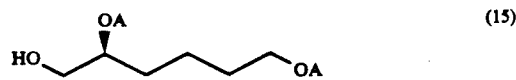

h) reaction with pyridinium chlorochromate to produce the aldehyde of formula:

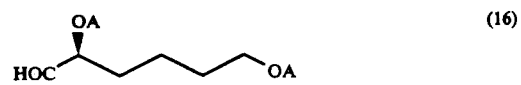

i) reaction with the compound of formula:

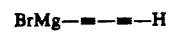

to produce the diacetylene compound of formula (8).

11. Sulphoxide of formula:

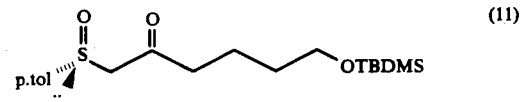

in which formula TBDMS represents the t-butyldimethylsilyl radical and tol the tolyl radical.

12. Sulphoxide of formula:

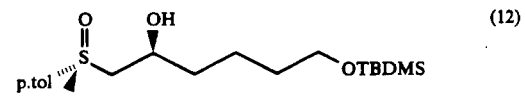

in which formula tol and TBDMS have the meanings given in claim 11.

13. Sulphoxide of formula:

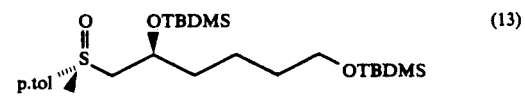

in which formula tol and TBDMS have the meanings given in claim 11.

14. Acetoxylated derivative of formula:

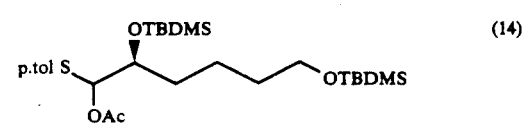

in which formula TBDMS and tol have the meanings given in claim 11 and Ac represents the acetyl radical.

15. Alcohol of formula:

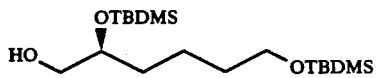
(15)

in which formula TBDMS represents the t-butyldimethylsilyl radical.

16. Aldehyde of formula:

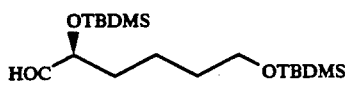
(16)

in which formula TBDMS represents the t-butyldimethylsilyl radical.

17. Diacetylene compound of formula:

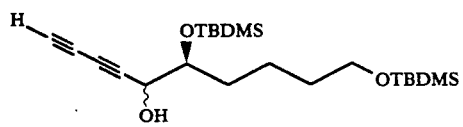
(8)

in which formula TBDMS represents the t-butyldimethylsilyl radical.

18. Diacetylene compound of formula:

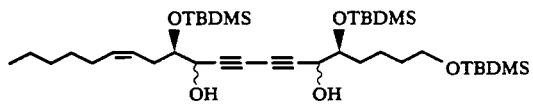
(7)

in which formula TBDMS represents the t-butyldimethylsilyl radical.

19. Butadienediol of formula:

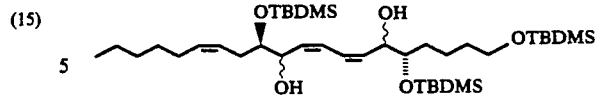
(2)

in which formula TBDMS represents the t-butyldimethylsilyl radical.

20. Dibenzoate of formula:

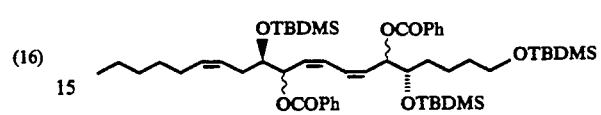
(3)

in which formula TBDMS represents th t-butyldimethylsilyl radical and Ph represents a phenyl radical.

21. Triether of formula:

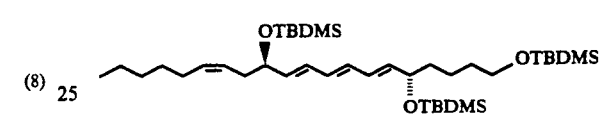
(4)

in which formula TBDMS represents the t-butyldimethylsilyl radical.

22. Triol of formula:

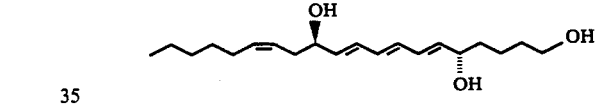
(5)

23. Lactone of formula:

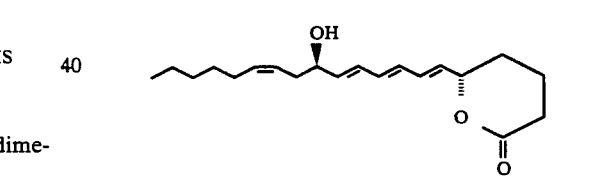
(6)

* * * * *